United States Patent [19]

Theeuwes et al.

[11] Patent Number: 4,876,093
[45] Date of Patent: * Oct. 24, 1989

[54] DISPENSER WITH DISPERSING MEMBER FOR DELIVERING BENEFICIAL AGENT

[75] Inventors: Felix Theeuwes, Los Altos; Patrick S. L. Wong, Hayward, both of Calif.

[73] Assignee: ALZA Corporation, Palo Alto, Calif.

[*] Notice: The portion of the term of this patent subsequent to Apr. 25, 2006 has been disclaimed.

[21] Appl. No.: 69,148

[22] Filed: Jul. 2, 1987

[51] Int. Cl.[4] .................. A61K 9/22; A61M 31/00
[52] U.S. Cl. .................... 424/438; 424/468; 424/469
[58] Field of Search ............ 424/438, 464, 466, 473, 424/468; 401/12

[56] References Cited

U.S. PATENT DOCUMENTS

| | | | |
|---|---|---|---|
| 2,893,032 | 7/1959 | Selmer | 401/12 |
| 3,995,632 | 12/1976 | Nakano et al. | 128/260 |
| 4,251,506 | 2/1981 | Laby | 424/19 |
| 4,327,725 | 5/1982 | Cortese et al. | 128/260 |
| 4,350,271 | 9/1982 | Eckenhoff | 222/386.5 |
| 4,408,919 | 10/1983 | Wolff et al. | 401/12 |
| 4,595,583 | 6/1986 | Eckenhoff et al. | 424/15 |
| 4,612,008 | 9/1986 | Wong et al. | 604/892 |

Primary Examiner—Nancy A. B. Swisher
Attorney, Agent, or Firm—Sabatine, Paul L.; Edward L. Mandell; Steven F. Stone

[57] ABSTRACT

A dispenser is enclosed for delivering a beneficial agent to an environment of use. The dispenser comprising a wall that surrounds an internal space comprising carrier means for housing a beneficial agent, push means for pushing the carrier means from the dispenser and fragmenting means for fragmenting the carrier means as it is pushed from the dispenser.

21 Claims, 2 Drawing Sheets

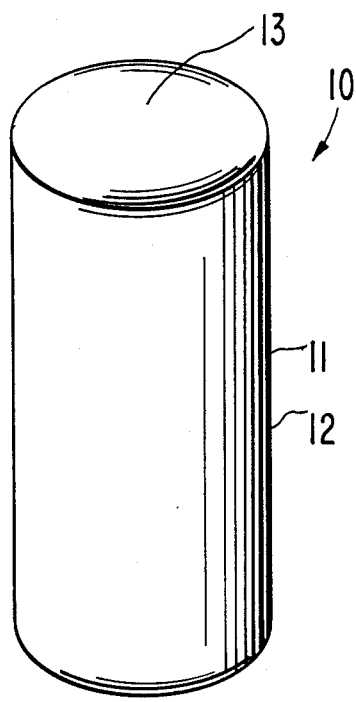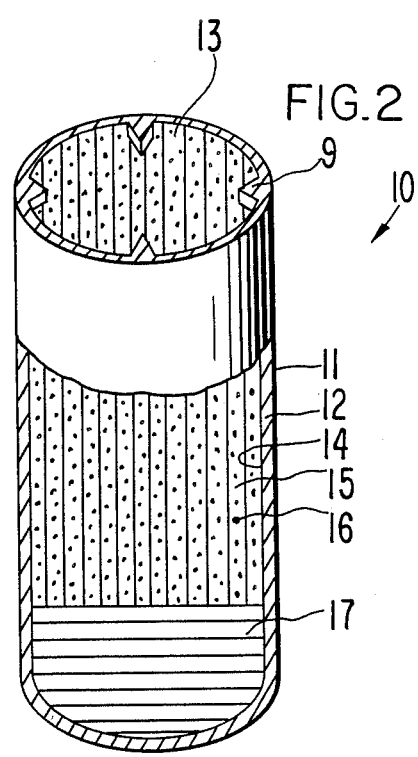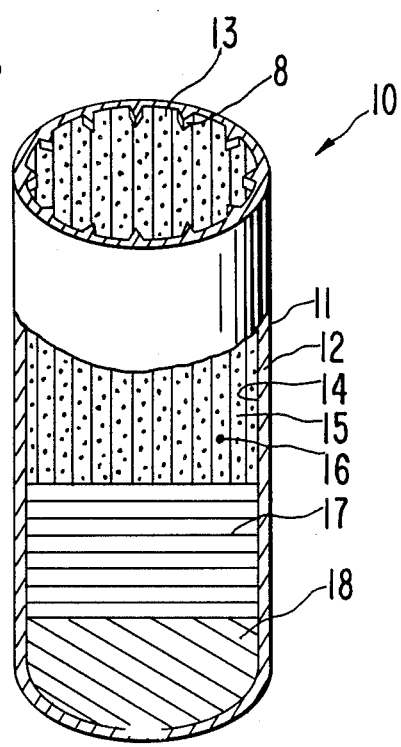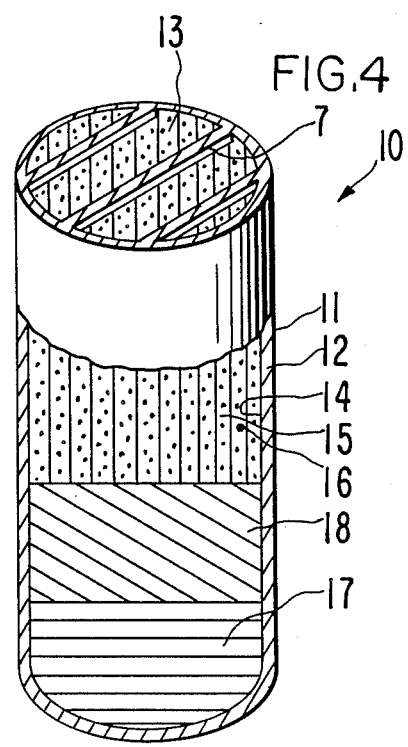

DISPENSER WITH DISPERSING MEMBER FOR DELIVERING BENEFICIAL AGENT

CROSS-REFERENCE WITH COPENDING APPLICATIONS

This application is copending with U.S. patent application Ser. No. 07/054,714 filed May 24, 1987 and now U.S. application Ser. No. 07/072,506 filed July 13, 1987.

FIELD OF THE INVENTION

This invention pertains to both a novel and useful dispenser for dispersing a beneficial agent into an environment of use. More particularly, the invention relates to a dispenser comprising a wall that surrounds a lumen comprising a matrix containing a beneficial agent, means for pushing the matrix towards an opening in the dispenser, and means at the opening for dispersing the matrix containing the beneficial agent into the environment of use.

BACKGROUND OF THE INVENTION

Dispensers useful for delivering a beneficial agent to an environment of use are known to the prior art. For example, one such dispenser is disclosed in U.S. Pat. No. 3,995,632 issued to Nakano, Higuchi and Hussain. This patent discloses a dispenser comprising a saturated solution of magnesium sulfate that pushes against a melted composition. The melted composition is squeezed through a small passageway from the dispenser. In U.S. Pat. No. 4,251,506 issued to Laby, a device is disclosed consisting of a controlled release composition for administering a therapeutic agent to a ruminant. The patent discloses a spring for pushing a meltable composition from the dispenser through a wide opened mouth. The use of a spring as a driving force limits the practical use of the device as the driving force of a spring decreases through the distance the spring operates. For this device, drug delivery decreases over time as the spring elongates and concurrently weakens. The delivery rate is influenced also by the nature of the composition and its interaction with fluid at the interfaced environment of use. The interface provides mechanical action that controls drug release by the environment and not by the device. Another dispenser is disclosed in U.S. Pat. No. 4,327,725 by Cortese and Theeuwes. The dispenser disclosed in this patent comprises a hydrogel that urges an aqueous formulation through a passageway from the dispenser. In U.S. Pat. No. 4,350,271 issued to Eckenhoff, a dispenser is disclosed comprising a water swellable composition that pushes a lipophilic fluid from the dispenser. U.S. Pat. No. 4,612,008 issued to Wong, Barclay, Deters and Theeuwes discloses a dispenser wherein an expanding polymer urges a drug formulation comprising an aqueous osmotically active solution from the dispenser. Another dispenser is disclosed by patentee Eckenhoff, Cortese and Landrau in U.S. Pat. No. 4,595,583. The dispenser disclosed in this patent comprises an expandable aqueous activated osmopolymer that urges a heat responsive composition through an orifice from the dispenser.

The dispenser of the prior art presented above represents an outstanding and pioneering advancement in the dispensing art, and they are additionally useful for dispensing innumerable beneficial agents to an environment of use. Now, this present invention has unexpectedly discovered that a dispenser can be provided comprising a novel and unobvious dispensing means unknown to the prior art for delivering a beneficial agent to an environment of use. That is, it has now been discovered that a dispenser can be provided comprising means for delivering a bio-affecting beneficial agent in a preferred substantially formulated solid form at a kinetically controlled rate substantially equal to its kinetic rate of release through a dispersing member from the dispenser. The dispenser thereby makes available to a beneficial agent receptor controlled and constant prolonged delivery of a beneficial agent according to a preselected, built-in optimal program of beneficial agent presentation.

OBJECTS OF THE INVENTION

Accordingly, in view of the above presentation, it is a principle object of this invention to provide a dispenser comprising means for the controlled delivery of a beneficial agent at a rate substantially equivalent to its dispenser-controlled rate of release from the dispenser over time.

Another object of the present invention is to provide a dispenser comprising means for dispersing a beneficial agent into an environment of use at a controlled rate from a dispenser over time.

Another object of the present invention is to provide a dispenser that delivers a beneficial agent in a solid state that is dispersed into a fluid environment of use as it is dispersed from the dispenser.

Another object of the present invention is to provide a dispenser comprising a beneficial agent in a solid state that erodes at a controlled rate in a fluid environment, and which dispenser comprises means for preventing a premature displacement of the solid state from the dispenser.

Another object of the present invention is to provide a dispenser that delivers a beneficial agent in a solid state carrier that diffuses from the carrier at a controlled rate after the carrier is dispensed through a dispersing means at a rate-displaced from the carrier into a fluid environment of use.

Another object of the present invention is to provide a dispenser comprising a carrier selected from the group consisting of a solid and semisolid containing a beneficial agent that is dispersed through a dispersion member into a fluid environment wherein the beneficial agent is leached from the carrier over time.

Another object of the present invention is to provide a dispenser comprising a carrier selected from the group consisting of a solid and semisolid carrier containing a beneficial agent that is dispersed from the dispenser with the beneficial agent delivered by osmotic bursting from the carrier into a fluid environment over time.

Another object of the present invention is to provide a dispenser comprising a carrier selected from the group consisting of an erodible solid carrier and an erodible semisolid carrier, which carrier in either instance contains a beneficial agent that is released by erosion of the carrier after the carrier is push-dispensed into a fluid environment of use.

Another object of the present invention is to provide a dispenser that is self-contained, self-starting, self-powered and self-dispersing of a beneficial agent in a fluid environment of use.

Another object of the present invention is to provide a dispenser that is easy to manufacture, economical to make, and can be used for dispersing a solid stick-like carrier into smaller parts containing a beneficial drug into an environment of use.

Another object of the present invention is to provide a dispenser comprising an internal lumen containing a carrier comprising a continuous, uninterrupted linear body member symmetrical with the axis of the lumen, and which carrier is displaced at a continuous, uninterrupted rate from the lumen and dispersed as a plurality of smaller carriers through a dispersing member over time.

Another object of the present invention is to provide a dispenser comprising a wall that surrounds a lumen with a mouth in the wall having an opening substantially equal to the cross-sectional area of the lumen, and which mouth contains a distribution member for dispersing the contents of the lumen into an environment of use.

Another object of the present invention is to provide a dispenser comprising a wall that surrounds a lumen with a mouth in the wall, a distribution member in the mouth as means for dispersing the contents of the lumen, and which lumen houses a continuous body member that is pushed through the distribution member and by so doing a solid formulation of insoluble drug up to 92% can be dispersed in a dispersible carrier to the environment of use.

Another object of the invention is to provide a dispenser comprising a wall that surrounds an internal lumen, which lumen contains a carrier that initially occupies a major portion of the lumen except for the space occupied by a driving member and an optional densifier, with the dispenser delivering a beneficial agent by the combined physical-chemical operations of the driving member urging the displaceable carrier through means for dispersing the carrier in the wall to the environment of use.

Another object of the invention is to provide a delivery system manufactured as a dispenser comprising a carrier for a drug wherein the carrier keeps its physical and chemical integrity during its stay in the dispenser and changes its physical and/or chemical integrity on its displacement through means for dispersing the carrier from the dispenser into a fluid environment of use.

Another object of the present invention is to provide a drug delivery system that can deliver a beneficial drug contained in a pharmaceutical carrier that maintains its structure within the delivery system and changes its structure after its delivery through a dispersing member into the gastrointestinal tract wherein the pharmaceutical carrier dispenses the drug.

Another object of the present invention is to provide a drug delivery system comprising a pharmaceutical carrier that is a dispensable, innocuous composition and when upon its displacement from the delivery system through means for dispersing and diffusing the carrier drug composition the composition substantially avoid mammalian tissue irritation and interaction with mammalian protein tissue.

Another object of the invention is to provide a drug delivery device for dispensing a drug to a ruminant, which delivery system comprises an inner lumen containing a nonmeltable and nonaqueous thermoplastic composition, a space occupying member, a density member, and which composition comprises from soluble to insoluble beneficial agents that can be dispensed by the thermoplastic composition after said thermoplastic composition exits through a diffusion member form the deliver device.

Other objects, features and advantages of the invention will be more apparent to those skilled in the dispensing art form the following detailed description of the specification taken in conjunction with the drawings and the accompanying claims.

BRIEF DESCRIPTION OF THE DRAWINGS

In the drawing figures which are not drawn to scale, but are set forth to illustrate various embodiments of the invention, the drawing figures are as follows:

FIG. 1 is a view of a dispenser designed and manufactured for administering a beneficial agent to a warm-blooded animal;

FIG. 2 is an opened view of the dispenser of FIG. 1 through the vertical length of the dispenser for illustrating the structure of the dispenser, wherein the dispenser comprises an internal lumen housing a pharmaceutically acceptable carrier that does not melt at the temperature of an animal body, which carrier comprises a continuous body member extending through a major length of the lumen, a space occupying means for pushing the continuous carrier from the lumen, and means for dispersing the carrier into smaller members as it leaves the lumen;

FIG. 3 is an opened view of the dispenser of FIG. 1 taken in conjunction with FIG. 2, wherein the dispenser depicts a carrier comprising a composition that is thermally stable at the temperature of an animal environment of use, a beneficial drug dispersed in the carrier, a dense member for keeping the dispenser in an environment of use, and means in the opening for fragmenting the carrier as it is pushed from the dispenser;

FIG. 4 is an opened view of the dispenser of FIG. 1 taken in conjunction with FIG. 2, wherein the dispenser depicts another arrangement of the push member and the dense member, and the dispenser comprise a different means for breaking-up the carrier as it is pushed through the opening in the wall of the dispenser;

In the drawing figures and in the specification like parts in related figures are identified by like parts. The terms appearing earlier in the specification and in the description of the drawings as well as embodiments thereof are further detailed elsewhere in the disclosure.

DETAILED DESCRIPTION OF THE DRAWING FIGURES

Figure 5:
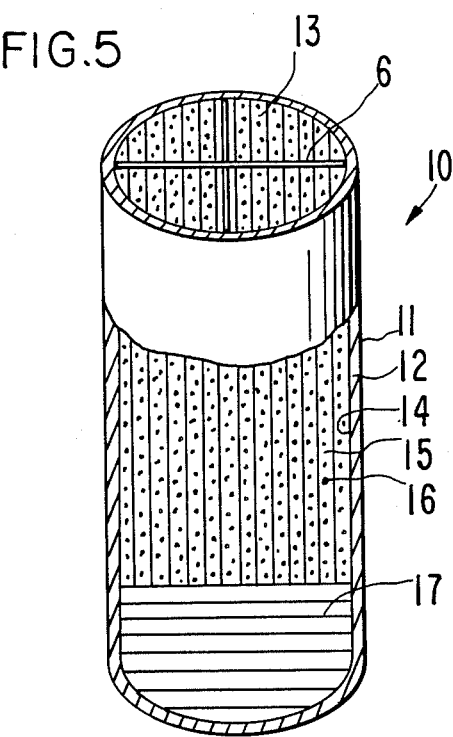
FIG. 5 is an opened view of a dispenser depicting a semipermeable wall that surrounds a lumen wherein a thermally stable carrier, as it leaves the lumen, is sectioned from the main body of the carrier on entering the environment of use.

Turning now to the drawing figures in detail, which are examples of new and useful dispensers for delivering a beneficial agent, and which examples are not to be construed as limiting, one example of a dispenser is depicted in FIG. 1 identified by the numeral 10. In FIG. 1, dispenser 10 comprises a body 11 comprising a wall 12 that surrounds and defines an internal lumen, not seen in FIG. 1. Body 11 formed of wall 12 defines and surrounds a wide-mouth opening 13 for delivering the contents of dispenser 10 to an environment of use.

FIG. 2 is an opened view of dispenser 10 for illustrating the structure of dispenser 10. Dispenser 10 of FIG. 1 comprises body 11, wall 12 and mouth 13. Wall 12 surrounds an internal lumen 14. In a presently preferred embodiment wall 12 comprises in whole, or at least in part, semipermeable wall forming composition that is substantially permeable to the passage of an external fluid, and wall 12 is substantially impermeable to the passage of a beneficial agent and other ingredients contained in dispenser 10. In another embodiment wall 12 can comprise a semipermeable composition and in part can comprise a different composition such as a polyolefin. Wall 12 is non-toxic and it maintains its physical and chemical integrity, that is, wall 12 does not erode during the dispensing life of dispenser 10. Wall 12 surrounds and defines an internal lumen 14. Lumen 14 contains carrier means 15 comprising a beneficial agent 16, represented by dots. Lumen 14 contains also a driving means 17 that is in layered contact with carrier means 15 for pushing carrier means 15 from dispenser 10.

In FIG. 2 a mouth in wall 12 connects the inside of dispenser 10 with inside lumen 14. Mouth 13 is a wide-mouth opening in wall 12, which opening 13 comprises a cross-section that is substantially equal to the internal cross-sectional dimensions of lumen 14. Wall 12, at opening 13, additional comprises at least one means 9 for breaking carrier 15 into smaller parts as carrier 15 is pushed by driving means 17 from lumen 14. Means 9 are inwardly projected and means 9 comprise any shape, such as a triangle, for breaking a solid or a semisolid carrier means 15 from a continuous state at the point of entry into the environment into a non-continuous state. Means 9 can be integrally formed in wall 12, or means 9 can be integrally molded from a suitable plastic material and fixed to wall 12 by heat, or provided by a mechanical crimp cap, glue, or the like.

FIG. 3 depicts dispenser 10 in another embodiment provided by the invention. Dispenser 10 in FIG. 3 comprises body 11, wall 12, mouth 13, lumen 14, pharmaceutically acceptable carrier means 15, beneficial agent 16 in pharmaceutically acceptable carrier 15 and space consuming or driving means 17. Pharmaceutically acceptable carrier means 15 keeps its integrity inside lumen 14, that is, it is nonmeltable and it does not disintegrate, dissolve or hydrolyze while carrier 15 is inside lumen 14. Space consuming member 17, in operation inside lumen 14, absorbs and or imbibes aqueous fluid through wall 12, thereby causing space consuming means 17 to continuously occupy additional space in lumen 14. This occupying of space in lumen 14 by means 17 causes means 17 to apply pressure against carrier 15 through opening 13. Opening 13 comprises a plurality of serrations 8 arranged like the teeth of a saw.

This saw-tooth arrangement fragments carrier 15 as it passes through the plurality of serrations 8. Dispenser 10 comprises also a dense member 18 or densifier that is an optional component of dispenser 10 for keeping dispenser 10 in the rumen of an animal over a prolonged period of time. In FIG. 3, lumen 14 houses pharmaceutical carrier means 15 in layered contact with a surface of space consuming means 17, which means 17 is in contact with densifier 18.

FIG. 4 depicts dispenser 10 comprising body 11, wall 12, opening 13, lumen 14, housing pharmaceutically acceptable carrier 15 containing beneficial agent 16, space consuming means 17 positioned distant from opening 13 and a dense member 18 positioned between carrier 15 and means 17 for occupying space in lumen 14. Opening 13 in dispenser 10 comprises at least one means 7, or a plurality of means 7, for cutting carrier 15 as it leaves lumen 13. Means 7 can comprise a cutting instrument such as a sharp blade fastened to wall 13, a knife-like wire, a microtone or the like. Carrier 15 as it is pushed through cutting means 7, is cut into a plurality of smaller carriers. The smaller carriers in the presence of aqueous-type biological fluid in the environment of use release beneficial agent 16 at a controlled rate by at least one process of erosion, leaching, osmotic bursting, or diffusion. Carrier 15 also can be made of a material that disintegrates, dissolves or hydrolyzes in the fluid environment of use. Dispenser 10 delivers its beneficial agent 16 at a controlled rate by the combined operation of carrier 15 releasing agent 16 and means 17 consuming space and pushing carrier 15 through cutting means 7 over time.

FIG. 5 illustrates another embodiment of dispenser 10. In FIG. 5, dispenser 10 comprises body 11, wall 12, opening 13, lumen 14, carrier 15, beneficial agent 16 and space consuming means 17. Opening 13 comprises a pair of thin blades 6 for slicing carrier 15 into sections as carrier 15 leaves lumen 14. The blades are made as knife edges fastened to wall 12, and they cut or break-up solid carrier 15 as it enters the environment of use. As carrier 15 leaves lumen 14 through knife edges 6, space consuming means 7 continuously pushes carrier 15 toward opening 13 thereby continuously presenting, at a controlled rate, carrier 15 to knife edges 6.

Figure 6:
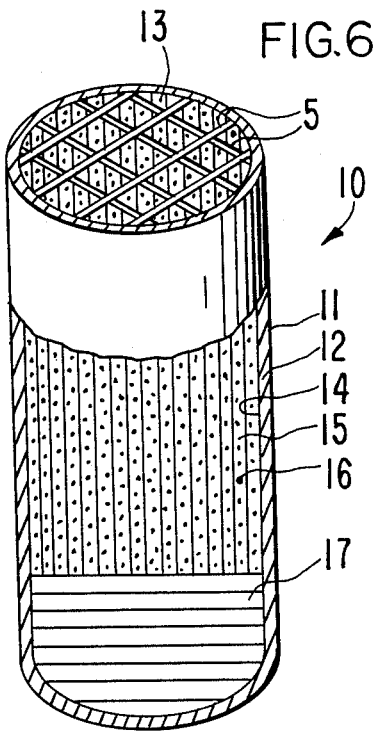
FIG. 6 is an opened view of a dispenser wherein the lumen of the dispenser comprises a carrier that is non-meltable at animal body temperatures, a beneficial agent in the carrier, means for occupying space in the lumen for pushing the carrier through a number of means for breaking-up the carrier position in the opening in the wall of the dispenser.

FIG. 6 illustrates another embodiment of dispenser 10 provided by the invention. In FIG. 6 dispenser 10 comprises body 11, wall 12, opening 13, lumen 14, carrier 15, beneficial agent 16, and space consuming means 17. Opening 13 comprises a plurality of knife edges 5 that cross, intersect or run counter or opposite to each other. The transverse edges 5 break carrier 15 into small pieces or into a plurality of carriers of smaller size for providing quicker delivery of beneficial agent 16 to an environment of use as carrier 15 is pushed from lumen 14.

Figure 7:
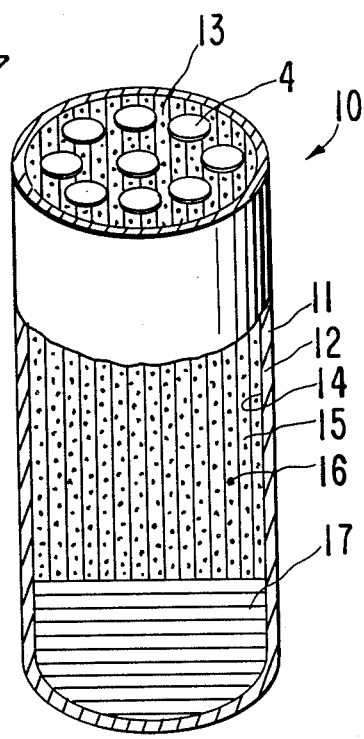
FIG. 7 is an opened view of the dispenser through the vertical length of the dispenser for illustrating the internal structure of the dispenser comprising a wall that maintains its physical and chemical integrity, a carrier that maintains its physical and chemical integrity inside the dispenser, and means for occupying space in the lumen for urging the carrier through a multiplicity of openings for extruding the carrier in a ribbon-like manner as the carrier leaves the dispenser; and, FIG. 8 is an opened view of the dispenser illustrating a carrier in the lumen, means for pushing the carrier through an opening in the wall of the dispenser, and means in the wall for preventing a premature ejection of the carrier from the dispenser.

FIG. 7 illustrates another embodiment of dispenser 10 provided by the invention. In FIG. 7 dispenser 10 comprises body 11, wall 12, opening 13, lumen 14, carrier 15, beneficial agent 16 and space consuming means 17. Opening 13 comprises a plurality of smaller openings 4 generally arranged in a shower head or a screen like arrangement. The shower head or screen breaks-up the solid formulation carrier 15 when emerging through larger opening 13.

Figure 8:
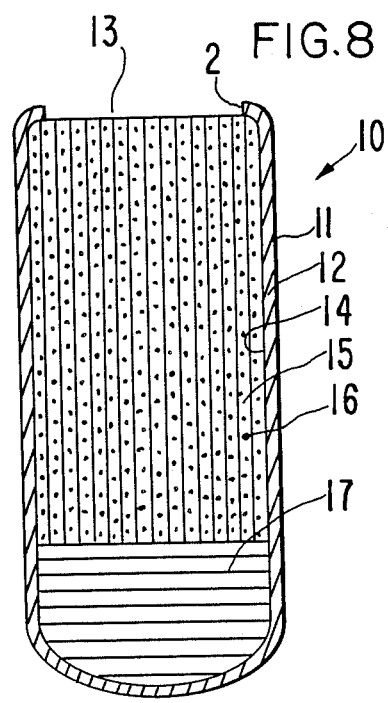

FIG. 8 illustrates another dispenser 10 provided by the invention. In FIG. 8, dispenser 10 is seen in opened section and it comprises body 11, wall 12, opening 13, lumen 14, carrier 15, beneficial agent 16 and space consuming mean 17. Dispenser 10 additionally comprises the improvement wherein wall 12 curves inward to provide means 2 for (a) breaking carrier 15 into small sections as carrier means 15 emerges from lumen 14, and for (b) aiding in avoiding a premature ejection of solid carrier means 15 from lumen 14. Means 2 ca be integrally formed in wall 12 during a coating process, or means 2 can be molded into wall 12 during injection molding process.

While FIGS. 1 through 8 are illustrative of various dispensers that can be made according to the invention, it is to be understood these dispensers are not to be construed as limiting, as dispenser 10 can take a wide variety of shapes, sizes and forms adapted for delivering a beneficial agent to different fluid environments of use. For example, dispenser 10 can be designed for use that includes implant, artificial gland, intrauterine, vagina, anal-rectal dispensers, and the like. Dispenser 10 can be used in veterinary clinics, farms, zoos, laboratories, on the range, in feed lots, in hospitals, birth clinics and other environments of use.

DETAILED DESCRIPTION OF THE INVENTION

In accordance with the practice of this invention it now has been found that dispenser 10 can be manufactured with a lumen that houses, in cooperative relationship, in lumen 14 carrier means 15, beneficial agent 16, space consuming means 17 and other optional embodiments such as densifier 18. Wall 12 of dispenser 10 is formed by wall 12 comprising a composition that does not adversely affect the carrier, the beneficial agent, the space consuming means, the density means, and other ingredients such as an osmagent, a gas generating couple, and the like, that can be housed in dispenser 10. Wall 12 is permeable, in at least a part, to the passage of an external fluid such as water and biological fluids, and it is substantially impermeable to the passage of beneficial agent, osmagents, osmopolymers, and the like. The wall comprises a material that does not adversely affect an animal, or host, or the components comprising the device, and the selectively semipermeable materials used for forming the wall are nonerodible and they are insoluble in fluids. Typical selectively semipermeable materials for forming wall 12 are, in one embodiment, cellulose esters, cellulose ethers and cellulose ester-ethers. These cellulosic polymers have a degree of substitution, D.S., on the anhydroglucose unit, from greater than 0 up to 3, inclusive. By degree of substitution is meant the average number of hydroxyl groups originally present on the anhydroglucose unit comprising the cellulose polymer that are replaced by a substituting group. Representative compounds include a member selected from the group consisting of cellulose acylate; cellulose diacetate; cellulose triacylate; cellulose acetate; cellulose diacetate; cellulose triacetate; mono, di- and tricellulose alkanylates; mono-, di- and tricellulose aroylates, and the like. Exemplary polymers include cellulose acetate having a D.S. up to 1 and an acetyl content up to 21%; cellulose acetate having an acetyl content of 32% to 39.8%; cellulose acetate having a D.S. of 1 to 2 and an acetyl content of 21% to 35%; cellulose acetate having a D.S. of 2 to 3 and an acetyl content of 35% to 44.8%, and the like. More specific cellulose polymers include cellulose propionate having a D.S. of 1.8 and a propyl content of 39.2% to 45% and a hydroxyl content of 2.8% to 5.4%; cellulose acetate butyrate having a D.S. of 1.8, an acetyl content of 13% to 15% and a butyryl content of 34% to 39%; cellulose acetate butyrate having an acetyl content of 2% to 29%, a butyryl content of 17% to 53% and a hydroxyl content of 0.5% to 4.7%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentanoate; co-esters of cellulose such as cellulose acetate butyrate and cellulose acetate propionate, and the like.

Additional polymers include ethyl cellulose of various degree of etherification with ethoxy content of from 40% t 55%; acetaldehyde dimethyl cellulose acetate; cellulose acetate ethyl carbamate; cellulose acetate methyl carbamate; cellulose acetate dimethyl aminoacetate; semipermeable polyamides; semipermeable polyurethanes; semipermeable sulfonated polystyrenes; semipermeable cross-linked selective polymers formed by the coprecipitation of a polyanion and a polycation as disclosed in U.S. Pat. Nos. 3,173,876; 3,276,586; 3,541,005; 3,541,006 and 3,546,142; semipermeable polymers as disclosed by Loeb and Sourirajan in U.S. Pat. No. 3,133,132; semipermeable light cross-linked polystyrene derivatives; semipermeable cross-linked poly(sodium styrene sulfonate); semipermeable cross-linked poly(vinylbenzyltrimethyl ammonium chloride); semipermeable polymers exhibiting a fluid permeability of $2.5 \times 10^{-11}$ to $2.5 \times 10^{-4}$ (cm/$^2$ hr. atm) expressed per atmosphere of hydrostatic, osmotic or inhibition pressure difference across the semipermeable wall. The polymers are known to the art in U.S. Pat. Nos. 3,845,770; 3,916,899 and 4,160,020; and in *Handbook of Common Polymers* by Scott, J. R. and Roff, W. J., 1971, published by CRC Press, Cleveland, OH.

Wall 12 can comprise an optional flux regulating agent. The flux regulating agent is a compound added to assist in regulating the fluid permeability or flux through the wall 12. The flux regulating agent can be a flux enhancing agent or a flux decreasing agent. The agent can be preselected to increase or decrease the liquid flux. Agents that produce a marked increase in permeability to fluid, such as water, are often essentially hydrophilic, while those that produce a marked decrease to fluids, such as water, are essentially hydrophobic. The amount of regulator in the wall when incorporated therein generally is from about 0.01% to 20% by weight, or more. The flux regulator agents in one embodiment that increase flux include polyhydric alcohols, polyalkylene glycols, polyalkylenediols, polyesters of alkylene glycols, and the like. Typical flux enhancers include polyethylene glycol 300, 400, 600, 1500, 4000, 6000 and the like; low molecular weight glycols such as polypropylene glycol, polybutylene glycol and polyamylene glycol; the polyalkylenediols such as poly(1,3-propanediol), poly(1,4-butanediol), poly(1,6-hexanediol), and the like; aliphatic diols such as 1,3-butylene glycol; 1,4-pentamethylene glycol; 1,4-hexamethylene glycol, and the like; alkylene triols such as glycerine, 1,2,3-butanetriol; 1,2,4-hexanetriol; 1,2,6-hexanetriol, and the like; ester such as ethylene glycol dipropionate; ethylene glycol butyrate; butylene glycol dipropionate; glycerol acetate esters, and the like. Representative flux decreasing agents include phthalates substituted with an alkyl and alkoxy, or with both an alkyl and alkoxy group such as diethyl phthalate, dimethoxyethyl phthalate, dimethyl phthalate, and [di(2-ethylhexyl) phthalate], aryl phthalates such as triphenyl phthalate, and butyl benzyl phthalate; insoluble salts such as calcium sulphate, barium sulphate, calcium phosphate, and the like; insoluble oxides such a titanium oxide; polymers in powder, granule and like forms such as polystyrene, polycarbonate, and polysulfone; esters such as citric acid esters esterfied with long chain alkyl groups; inert and substantially water impermeable fillers; resins compatible with cellulose based wall forming materials, and the like.

Other materials that can be used to form the wall 12 for imparting flexibility and elongation properties to the wall, for making wall 12 less-to-nonbrittle and to render tear strength include phthalate plasticizers such as dibenzyl phthalate, dihexyl phthalate, butyl octyl phthalate, straight chain phthalates of six to eleven carbons, di-isononyl phthalate, di-isodecyl phthalate, and the like. The plasticizers include nonphthalates such as triacetin, dioctyl azelate, epoxidized tallate, tri-isoctyl trimellitate, tri-issononyl trimellitate, sucrose acetate isobutyrate, epoxidized soybean oil, and the like. The amount of plasticizer in a wall when incorporated therein is about 0.01% to 20% by weight, or higher.

Representative of means 17 for manufacturing space consuming means 17 for urging pharmaceutical carrier means 15 from lumen 14 through mouth 13 are at least one of a member selected from the group consisting of an osmopolymer, an osmagent and a gas generating couple. Exemplary of an osmopolymer that can be used for the present purpose is a hydrogel. The hydrogel in the dispenser comprises a shape that corresponds to the internal shape of lumen 14. The hydrogel composition is noncross-linked or optionally cross-linked and it possesses osmotic properties such as the ability to imbibe an exterior fluid through semipermeable wall 12, and exhibit an osmotic pressure gradient across semipermeable wall 12 against a fluid outside dispenser system 10. The materials used for forming the space consuming member that are swellable and expandable are polymeric materials neat, and polymeric materials blended with osmotic agents that interact with water or biological fluid, absorb the fluid and swell or expand to an equilibrium state. The polymer exhibits the ability to retain a significant fraction of imbibed fluid in the polymer molecular structure. The polymers in a preferred embodiment are gel polymers that can swell or expand to a very high degree, usually exhibiting a 2 to 50 fold volume increase. The swellable, hydrophilic polymers, also known as osmopolymers, can be on cross-linked or lightly cross-linked. The crosslinks can be covalent or ionic bonds with the polymer possessing the ability to swell in the presence of fluid, and when cross-linked it will not be dissolved in the fluid. The polymer can be of plant, animal or synthetic origin. Polymeric materials useful for the present purpose include poly(hydroxylalkyl methacrylate) having a molecular weight of from 5,000 to 5,000,000; poly(vinylpyrrolidone) having a molecular weight of from 10,000 to 360,000; anionic and cationic hydrogels; poly(electrolyte) complexes; poly(vinylalcohol) having a low acetate residual; a swellable mixture of agar and carboxymethyl cellulose; a swellable composition comprising methyl cellulose mixed with a sparingly cross-linked agar; a polyether having a molecular weight of 10,000 to 6,000,000; a water swellable copolymer produced by a dispersion of finely divided copolymer of maleic anhydride with styrene, ethylene, propylene or isobutylene; water swellable polymer of N-vinyl lactams, and the like.

Other gelable, fluid imbibing and fluid retaining polymers useful for forming the hydrophilic, expandable push member include pectin having a molecular weight ranging from 30,000 to 300,000; polysaccharides such as agar, acacia, karaya, tragacanth, algins and guar; Carbopol ®, an acrylic acid polymer; a carboxyvinyl polymer, sometimes referred to as carboxypolymethylene; a polymer of acrylic acid cross-linked with a polyallyl ether of sucrose as described in U.S. Pat. Nos. 2,789,053 and 2,909,462 and available as Carbopols ® 934, 940 and 941 and its salt derivatives; polyacrylamides; water swellable indene maleic anhydride polymers; Goodrite ® polyacrylic acid having a molecular weight of 80,000 to 200,000; Polyox ® polyethylene oxide polymers having a molecular weight of 100,000 to 5,000,000; starch graft co-polymers; Aqua-Keep ® acrylate polymers with water absorbability of about 400 times its original weight; diesters of polyglucan; a mixture of cross-linked polyvinyl alcohol and poly(N-vinyl-2-pyrolidone); zein available as prolamine; poly(ethylene glycol) having a molecular weight of 4,000 to 100,000 and the like. In a presently preferred embodiment the expandable member is formed from polymers and polymeric compositions that are thermoformable. Representative polymers possessing hydrophilic properties are known in U.S. Pat. Nos. 3,865,108; 4,002,173; 4,207,893; 4,327,725 and in *Handbook of Common Polymers*, by Scott and Roff, published by Cleveland Rubber Company, Cleveland, OH.

The osmagent that can be used for the purpose of providing space consuming means 17 comprise inorganic and organic compounds that exhibit an osmotic pressure gradient against an external fluid across semipermeable wall 12. Osmagents also are known as osmotically effective compounds and as osmotically effective solutes. The osmagent imbibes fluid from the outside of dispenser 10 into lumen 14 causing the osmagent to produce a solution or a suspension that continuously occupies more space in lumen 14. As more fluid is imbibed into lumen 14 it exerts a pressure against pharmaceutically acceptable carrier 15 pushing it from dispenser 10. Osmotically effective compounds useful for the present purpose include inorganic and organic salts, polysaccharides, carbohydrates and the like. Representative solutes include magnesium sulfate, magnesium chloride, sodium chloride, potassium chloride, lithium chloride, potassium sulfate, sodium carbonate, sodium sulfate, lithium sulfate, sodium sulfate, potassium acid phosphate, calcium lactate, tartaric acid, lactose, fructose, mannitol, sorbitol, and mixtures thereof. The osmotically active compound is initially present in lumen 14 in excess and it can be in particle, crystal, pellet, powder or granule form. The osmotic pressure of an osmotic compound can be measured with a commercially available osmometer identified as Vapor Pressure Osmometer, Model 2B, available from Hewlett-Packard, Avondale, PA. The osmotic pressure in atmospheres of osmagents suitable for this invention will be greater than zero atm, generally from zero atm up to 500 atm, or higher.

The osmotically effective compound that can be blended homogeneously or heterogeneously with the swellable polymer to form a driving means 17 are the osmotically effective solutes that are soluble in fluid, imbibe fluid into the swellable polymer, and exhibit an osmotic pressure gradient across the semipermeable wall against an exterior fluid. Osmotically effective osmagents useful for the present purpose include magnesium sulfate, magnesium chloride, sodium chloride, lithium chloride, potassium sulfate, sodium sulfate, mannitol, urea, sorbitol, inositol, sucrose, glucose, and the like. The osmotic pressure in atmospheres, atm, of the osmagents suitable for the purpose of this invention will be greater than zero atm, generally from greater than zero atm up to 500 atm, or higher. The swellable, expandable polymer, in addition to providing a driving means 17 for pushing carrier 15 containing beneficial agent 16 from dispenser 10, further serves to function as a supporting matrix for an osmotically effective solute. The osmotic solute can be homogeneously or heterogeneously blended with the polymer to yield the desired expandable driving member 17. The composition in presently preferred embodiment comprises at least one polymer and at least one osmotic solute. Generally a composition will comprise about 20% to 90% by weight of polymer and 80% to 10% by weight of osmotic solute, with a presently preferred composition comprising 35% to 75% by weight of polymer and 65% to 25% by weight of osmotic solute.

The gas generating couple operable as space occupying means 17 is, in a presently preferred embodiment, an effervescent couple or composition. The gas generating couple comprises at least one preferably solid acidic material and preferably solid basic material that dissolve and react in aqueous fluid that enters the dispenser to produce carbon dioxide. The gaseous generation of carbon dioxide leads to the volume displacement of carrier 15 containing beneficial agent 17 from dispenser 10. The gas generating couple can be present in powder, crystalline, granular or compressed forms, and the like. The acidic compounds or acids that can be used include organic acids such as malic, fumaric, tartaric, itaconic, maleic, citric, adipic, succinic and measconic, and the corresponding anhydride such as itaconic anhydride and citriconic anhydride. Also inorganic acids such as sulfamic or phosphoric, and the like, can be used for gas generation. Acid salts such as the salts of organic foods can be used including monosodium citrate, potassium acid tartrate and potassium bitartrate. The basic compounds include metal carbonate and bicarbonate salts such as alkali metal carbonates and bicarbonates, or alkaline earth carbonates and bicarbonates. Exemplary materials include the alkali metals lithium, sodium, and potassium carbonate and bicarbonate, and the alkaline earth compounds magnesium and calcium carbonate or bicarbonate. Also useful are ammonium carbonate, ammonium bicarbonate and ammonium sesquecarbonate. The combination of certain of these acids and bases results in a more rapid gas production or effervescence when contacted by water. In particular, either citric acid or a mixture of citric acid and tartaric acid and sodium bicarbonate give a rapid gaseous reaction that can be used for urging carrier means 15 from dispenser 10. It will be understood the amount of acidic and basic material in a couple can vary over a wide range to satisfy the amount of gas generation needed to urge carrier means 15 from dispenser 10. The essentially anhydrous or dry couple is preferably substantially stoichiometrically balanced to produce a combination that generates carbon dioxide. Also, the acid and base materials can be used in any convenient proportion between 1 to 200 parts and 200 to 1 part on a weight basis to produce the desired results. In addition, the gas generating material can be a member that generates gas on contact with water such as a member selected from the group consisting of calcium carbide and carbure.

In a presently preferred embodiment pharmaceutically acceptable carrier means 15 maintains its physical and chemical integrity inside lumen 14, as used for the purpose of this invention, denotes a carrier formulation that does not substantially undergo change in lumen 14 or dispenser 10. That is, carrier formulation 15 does not hydrolyze, erode, disintegrate or dissolve in lumen 14 during operation of dispenser 10. The expression "non-meltable", as used for the present purpose, generally mean carrier 15 does not substantially melt inside lumen 14 of dispenser 10. That is, carrier means 15 inside lumen 14 substantially does not change from a solid to a liquid state in lumen 14. Carrier means 15, in its delivery from dispenser 10 into a fluid biological environment of use, such as the gastrointestinal tract of a warm-blooded animal, can undergo hydrolysis in the acidic or basic pH of the tract, it can undergo surface erosion, disintegration, dissolution, be hydrolyzed by enzymes, digested by bacteria or fungi, and the like.

Exemplary of carrier formulation means 15 generically include a member selected from the group consisting of a polyester, polylactide, polyacetal, polyorthoester, polyorthocarbonate, and the like.

Representative of more specific carrier formulation means 15 include a member selected from the group consisting of polyglycolic acid exhibiting a Tm of 230° C., where Tm is the melting point; polydiglycolide having a Tm of 230° C; polylactic acid having a Tm of 180° C; polydilactide having a Tm of 180° C; polydimethylglycolic acid with a Tm of 240° C; polycaprolactone having a Tm of 63° C; polyalkylene adipate wherein the alkylene group comprises 10 carbons having a Tm of 77° C; polylactide-co-glycolide, and the like.

Representative of additional compositions for forming carrier means 15 comprise polyanhydrides, polyanhydride polymers of sebacic and azalaic acid, hydrophobic polycarbolyic acids having one ionizable carboxylic hydrogen for each 8 to 22 total carbon atoms, bioerodible polymers that innocuously disintegrate or breakdown as a unit structure on release by dispenser 10 such as hydrophobic polycarboxylic acid having a repeating backbone unit of 8 to 22 carbon atoms for each pendant carboxylic hydrogen; a bioerodible polyvalent ion crosslinked polyelectrolyte with a polyvalent ion selected from the group consisting of aluminum, barium, cadmium, calcium, copper, iron and zinc with the polyelectrolyte selected from the group consisting of carrageenan, pectic acid, pectinic acid and the like; a polyester of the formula [—O—W—OC]y wherein W is an alkylene of 1 to 4 carbons and y is a whole number to provide a polymer having a molecular weight of 4,000 to 100,000; a polyorthoester selected from the group consisting of poly(2,2-dioxo-trans-1,4-cyclohexane dimethylene tetrahydrofuran), poly(2,2-dioxo-1,6-hexamethylene tetrahydrofuran), poly(1,4-cyclohexane dicarbinyl-2,2-dioxtetrahydrofuran), poly(2,2-dioxohexamethylene-1,3-dioxolane), poly(2,2,-dioxa-trans-2-methyl-cyclohexane-1,4-diethylene-2-pyrrolidone), poly(2,2-dioxa-us, trans-1,4-cyclohexane-dimethylene-2-thiocane), and the like. Representative of additional compositions for forming carrier means 15 include polyamino acid, polypeptide, polyglutamate, polygutamic acid, polylysine, and the like.

Representative of additional polymeric materials for providing carrier means 15 are a hydrophilic copolymer selected from the group consisting of poly(alginate), poly(carrageenan), poly(guar gum), poly(guar agar), poly(gum agar), poly(gum arabic), poly(gum ghatti), poly(gum paraya), poly(gum tragacanth), poly(tamarid gum), poly(xanthan gum), and the like. The hydrophilic polymeric material, when used for carrier means 15 comprises a different polymeric composition when a hydrophilic polymeric material is used for space consuming means 17, or when carrier means 15 and space consuming means 17 are in contact with each other.

In an additional operative embodiment carrier means 15 can be manufactured by compressing water insoluble materials selected from group (1) below into a shape that corresponds to the internal shape of lumen 14. For example, carrier means 15 can comprise a tableted, an elongated stick-like shape, or the like. Carrier means 15, in its additional operative embodiments, maintains its integrity in lumen 14 and on its exit from dispenser 10 disintegrates, or the like, in the fluid environment of use. In this manufacture, examples of group (1) can comprise a member selected from the group consisting of polymerized particulate compositions of matter comprising polyethylene, polypropylene, cellulose acetate, ethylcellulose, polysulfone, cellulose acetate butyrate, microcrystalline cellulose, and the like.

Carrier means 15, in another embodiment, can be manufactured from a member selected from group (2) substantially comprising insoluble organic and inorganic substances. Carrier 15, in this embodiment, keeps its shape in lumen 14, but loses its shape in an environment of use. Representative of insoluble organic and insoluble inorganic solids used for this purpose comprise a member selected from the group consisting essentially of calcium carbonate, calcium sulfate, diatomaceous earth, clay, silicon dioxide, and the like.

A carrier means 15, with operative properties, can be manufactured in one embodiment with good properties for engaging in contacting relationship with the inside of wall 12, by compounding a member selected from groups (1) with a member selected from group (2). For example, materials selected from (1) and (2) are mixed with each other and with an optional lubricant, high molecular weight hydrophobic solid, or an oil, and the like, and then with a small quantity of a member selected from the group consisting of a swellable polymer such as gelatin, hydroxypropylmethylcellulose, pectin, and the like, and with a disintegrating agent such as solka floc, pharmacological binders, and the like. The presence of the disintegration agent in carrier 15, on carrier 15's exposure to the environment of use, results in the break-up of carrier 15 into small parts with a concurrent delivery of beneficial agent 16 to the environment of use.

The expression "active agent 16", as used herein, includes any beneficial agent, or beneficial compound that can be delivered from dispenser 10 to produce a beneficial and useful result. The agent can be insoluble to very soluble in the pharmaceutically acceptable carrier means 15. The term "active agent", includes algicide, antioxidant, air purifier, biocide, bactericide, catalyst, chemical reactant, disinfectant, fungicide, fermentation agent, fertility inhibitor, fertility promoter, germicide, plant growth promoter, plant growth inhibitor, drug, preservative, rodenticide, veterinary drug, sterilization agent, sex sterilant, and the like.

In the specification and the accompany claims the term "beneficial agent 16" also includes drug. The term "drug" includes any physiologically or pharmacologically active substance that produces a local or systemic effect in animals, including warm-blooded mammals; humans and primates; avians; household, sport and farm animals; laboratory animals; fishes, reptiles and zoo animals. The term "physiologically", as used herein, denotes the administration of a drug to produce generally normal levels and functions in the environment of use. The term "pharmacologically" denotes generally variations in response to the amount of drug administered to the host. See *Stedman's Medical Dictionary*, 1966, published by Williams and Witkins, Baltimore, MD.

The active drug that can be delivered includes inorganic and organic compounds without limitation, including drugs that act on the peripheral nerves, adrenergic receptors, cholinergic receptors, nervous system, skeletal muscles, cardiovascular system, smooth muscles, blood circulatory system, synaptic sites, neuroeffector junctional sites, endocrine system, hormone systems, immunological systems, reproductive systems, skeletal system, autacoid system, alimentary and excretory systems, inhibitory of autocoid systems and histamine systems. The active drug that can be delivered for acting on these recipients include anticonvulsants, analgesics, antiParkinsons, anti-inflammatoiries, calcium antagonists, anesthetics, antimicrobials, antimalarials, antiparasites, antihypertensives, antihistamines, antipyretics, alpha-adrenergic agnoist, alpha-blockers, biocides, bactericides, bronchial dilators, beta-adrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, opthalmics, psychic energizers, parasympathomimetics, sedatives, sympathomimetics, tranquilizers, urinary tract drugs, vaginal drugs, vitamins, nonsteroidal anti-inflammatory drugs, angiotensin converting enzymes, polypeptide drugs, and the like.

Exemplary drugs that are very soluble in water and can be delivered by the dispenser of this invention include prochlorperazine edisylate, ferrous sulfate, aninocaproic acid, potassium chloride, mecamylamine hydrochloride, procainamide hydrochloride, amphetamine sulfate, benzphetamine hydrochloride, isoproteronol sulfate, methamphetamine hydrochloride, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, cimetidine hydrochloride, theophylline cholinate, cephalexin hydrochloride, and the like.

Exemplary drugs that are poorly soluble in water and that can be delivered by the dispenser of this invention include diphenidol, meclizine hydrochloride, prochlorperazine maleate, phenoxybenzamine, thiethylperazine maleate, anisindone, diphenadione erythrityl tetrantrate, digoxin, isoflurophate, acetazolamide, methazolamide, bendroflumethiazide, chlorpropamide, tolazamine, chlormadione acetate, phenaglycodol, allopurinol, aluminum aspirin, methotrexate, acetyl sulfisoxazole, erythromycin, progestins, esterogenic, progestational, corticosteroids, hydrocortisone, dydrocortiocosterone acetate, cortisone acetate, triamcinolone, methyltesterone, 17 beta-estradiol, ethinyl estradiol, ethinyl estradiol 3-methyl ether, pednisolone, 17 betahydroxyprogesterone acetate, 19-nor-progesterone, norgesterone, norethynodrel, and the like.

Examples of other drugs that can be delivered by the dispenser include aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, pivaloyloxethyl ester of alpha-methyldopa hydrochloride, theophylline, calcium gluconate, ketoprofen, ibuprofen, cephalexin, erthromycin, haloperidol, zomepirac, ferrous lactate, vincamine, diazepam, phenoxybenzamine, diltiazem, milrinone, captopril, madol, quanbenz, hydrochlorothiazide, ranitidine, flurbiprofen fenbufen, fluprofen, tolmetin, alolfenac, mefenamic, flufenamic, difuninal, nimodipine, nitrendipine, nisoldipine, nicardipine, felodipine, lidoflazine, tiapamil, gallopamil amlodipine, mioflazine, lisinolpril, enalapril, captopril, ramipril, endlapriat, famotidine, nizatidine, sucralfate, etintidine, tertatolol, minoxidil, chlordiazepoxide, chlordiazepoxide hydrochloride, diazepan, amitriptylin hydrochloride, ipramine hydrochloride, imipramine pamoate, and the like. The beneficial drugs are known to the art in *Pharmaceutical Sciences,* 14th Ed., edited by Remington, (1979) published by Mack Publishing Co., Easton, PA; *The Drug, The Nurse, The Patient, Including Current Drug Handbook,* by Falconer, et al, (1974–1976) published by Saunder Company, Philadelphia, Pa.; *Medicinal Chemistry,* 3rd Ed., Vol. 1 and 2, by Burger, published by Wiley-Interscience, New York; and in *Physicians' Desk Reference,* 38th Ed., (1984) published by Medical Economics Co., Oradell, N.J.

The term "beneficial agent 16", as used herein, also comprises medicines or drugs, nutrients, vitamins, food supplements and other agents that are administered to farm animals. The dispenser 10 can house other agents that are administered to farm animals. The dispenser 10 can house various amounts of beneficial agent for administering to a farm animal. A single dispenser can be administered to a farm animal, for example to a ruminant, or more than one dispenser can be administered to a ruminant during a therapeutic program.

Representative of beneficial medicaments 16 that can be dispensed to a farm animal using the delivery system 10 of this invention include anthelmintics such as benzimidazole, mebendazole, levamisole, albendazole, cambendazole, fenbendazole, parbendazole, oxfendazole, oxybendazole, thiabendazole, tichlorfon, praziquantel, thiophante, morantel, morantel tartrate, pyrantel, pyrantel tartrate, methoprine, and the like., antiparasitic agents for the management of endopharasites and ectoparasites, such as avermectin and ivermectin, as disclosed in U.S. Pat. Nos. 4,199,569 and 4,389,397 both assigned to Merck & Co., and in *Science,* Vol. 221, pp 823–828, (1983), wherein said ivermectin antiparasitic drugs are disclosed as useful for aiding in controlling commonly occurring infestations in farm animals, such as roundworms, lung worms and the like; and said ivermectin also being used for the management of insect infestation such as grub, lice, mange mite, mite, ticks, larve, flies such as larve warble fly, dung-breeding fly, larve and flies in the excreta of animals, and the like; with delivery system administering from 5 micrograms per kilogram per day (5 $\mu$g/kg/d), to 250 milligrams per day (250 mg/kg/d) to cattle for establishing avermectin, including ivermectin, blood levels; antimicrobial agents such as chloretetracycline, oxytetracycline, tetracycline, streptomycin, dihydrostreptomycin, bacitracins, erythromycin, chlortetracycline, ampicillins, penicillin, cephalosporins, and the like; sulfa drugs such as sulfa drugs such as sulfamethazine, sulfathiazole, sulfonamides, and the like; macrolides such as erythromycin, spiramycin, tylosin, and the like; nitrofurans; antibiotics; ionophores such as virginanyin, lasalocid, salinomycin, and the like; growth stimulants such a Monesin ® sodium and Elfazepam ® ; defleaing agents such as dexamethasone and flumethasone; rumen fermentation manipulators; antibloat agent such as organo-polysiloxanes; growth promoting agents; minerals, mineral salts and trace elements; formulations such as magnesium, copper, cobalt, iron, manganese, molybdenum, zine, selenium, copper oxide, copper sulfate, cobalt salt, copper salt, selenium salt, selenium disulfied, sodium selenite, inorganic trace elements, organic trace elements, cobalt oxide, and the like; hormone growth supplement such as stilbestrol; growth efficiency factors; beta-agonist such as denbuterol; vaccines such as bovine diarrhea vaccine; vitamins such as vitamin A, the B-group, C, D, E, K and the like; antienteritis agents such as furazolidone; nutritional supplements such as lysine, lysine monhydrochloride, methionine, mexhionine salts, amino acids, peptides and the like; beneficial alpha agonists and the like.

The drug can be in various forms such as uncharged molecules, molecular complexes, pharmacologically acceptable salts such as hydrochloride, hydrobromide, sulfate, laurate, palmitate, phosphate, nitrite, borate, acetate, maleate, tartrate, oleate and salicylate. For acidic drugs, salts of metals, amines or organic cations; for example, quarternary ammonium can be used. Derivatives of drugs such as ester, ethers and amides can be used. Also, a drug that is water insoluble can be used in a form that is a water soluble derivative thereof to serve as a solute, and on its release from the device is converted by enzymes, hydrolyzed by body pH or other metabolic processes to the original biologically active form. The amount of beneficial agent 16 in dispenser 10 adapted for human therapy generally is about from 0.05 ng to 10 g or more, with individual dispensers containing, for example, 25 ng, 1 mg, 5 mg, 10 mg, 25 mg, 125 mg, 250 mg, 500 mg, 750 mg, 1.0 g, 1.2 g, 1.5 g, 4.5 g, 7.5 g and the like, for administering to a human over time. The amount of beneficial agent 16 in dispenser 10 for veterinary therapy is usually from 75 ng to 50 g for farm animals, for example, 75 ng, 1 mg, 5 mg, 100 mg, 250 mg, 500 mg, 750 mg, 1.5 mg, 2 g, 5 g, 10 g, 25 g, and the like. Dispensers can be provided that have a rate of release from 5 micrograms to 5 grams per day, or higher, for a farm animal.

A rumen-retentive dispenser 10 can be manufactured in a variety of sizes and shapes for administering beneficial agent 10 to a ruminant animal. One presently preferred shape is an elongated or lengthened shape such as a cylinder-like shape, or a capsule with a wide-opened mouth. For example, for use with sheep dispenser 10 can embrace an elongated shape and have a diameter of about 0.5 inches to 1 inch (1.3 cm to 2.5 cm) and a length of about 0.5 inches to 4 inches (1.3 cm to 10 cm). For use with cattle dispenser system 10 comprises a diameter of about 0.5 inches to 1.5 inches (1.3 cm to 3.8 cm), and a length of about 1 inch to 6 inches (2.5 cm to 15 cm).

Pharmaceutically acceptable carrier means 15 on leaving lumen 14 of dispenser 10 delivers a beneficial agent 16 to a gastrointestinal tract of a human or an animal by rate controlled kinetics. For example, the pharmaceutical carrier means 15 can deliver a beneficial agent 16 as a rate controlled by diffusion, by osmosis, by osmotic bursting, by solution leaching, by solubilization by cross-link cleavage, by solubilization of carrier means 15, by hydrolysis, by solubilization of carrier means 15 by ionization of pendant groups, by solubilization of carrier means 15 by protonation of pendant groups, by solubilization by backbone cleavage, by biodegradation, by bioerosion, by enzymatic action, by oxidation, by reduction, by proteolysis, by displacement, by dissolution, by disintegration, and the like.

The density member 18, also referred to as densifier 18, used in dispenser 10 is dense enough to retain dispenser 10 in the rumenreticular sac of a ruminant. Density member 18 lets dispenser 10 remain in the rumen over a prolonged period of time rather than letting it pass into the alimentary tract and be eliminated therefrom. As system 10 remains in the rumen, beneficial active agent 16 is delivered by system 10 at a controlled rate to the ruminant over time. Generally, dense member 18 will have a density of from about 0.8 to 8, or higher, with the density in a presently preferred embodiment exhibiting a specific gravity of from 1.2 to 7.6. For the ruminants, cattle and sheep, it is presently preferred dense member 18 exhibit a density such that there is a resulting system density of about 3 gm/ml. Materials that have a density that can be used for forming dense member 18 include iron, iron shot, iron shot coated with iron oxide, iron shot magnesium alloy, steel, stainless steel, copper oxide, a mixture of cobalt oxide and iron powder, and the like. Dense member 18 in delivery system 10 can embrace different embodiments. For example, dense member 18 can be machined or cast as a single, solid piece made of stainless steel having a density of 7.6 gm/ml. The solid member 18 is made having a curved shape that corresponds to the internal shape of system 10. The solid can have an axially aligned bore that extends through the length of the unit member. In another embodiment dense means 18 can comprise a plurality of dense pellets or dense lamella. Density member 18 as described above consists of means having a specific gravity greater than the fluid environment of use for keeping dispenser 10 in the fluid environment over time.

The semipermeable wall forming composition can be applied to the exterior surface of a dispenser alone or in laminar arrangement by molding, air spraying, dipping or brushing with a semipermeable wall forming composition. Other and presently preferred techniques that can be used for applying the semipermeable wall ar the air suspension procedure and the pan coating procedures. The air procedure consists in suspending and tumbling the lumen forming components in a current of air and a semipermeable wall forming composition until the wall surrounds and coats the components. The procedure optionally can be repeated with a different semipermeable wall forming composition to form a semipermeable capsule laminated wall. The air suspension procedure is described in U.S. Pat. No. 2,799,241; *J. Am Pharm. Assoc.*, Vol. 48, pp 451-459, (1979) and *ibid*, Vol. 49, pp 82-84, (1960). Other standard manufacturing procedures are described in *Modern Plastics Encyclopedia*, Vol. 46, pp 62-70, (1969); and in *Pharmaceutical Sciences*, by Remington, 14th Ed., pp 1626-1678, (1970) published by Mack Publishing Co., Easton, PA. In those manufactures wherein the wall is coated by air suspension or by pan coating techniques, mouth 13 is formed in wall 12 by laser cutting, milling, sawing, drilling, injection molding, and the like. The manufacture of mouth 13 and the means for breaking-up carrier 15 can be effected when the device, or a cutting tool is in motion or stationary.

Exemplary solvents suitable for manufacturing the wall 12 include inert inorganic and organic solvents that do not adversely harm the materials, the capsule wall, the beneficial agent, the carrier composition, the expandable member, the dense member, and the final dispenser. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol isopropyl alcohol, butyl alcohol, methyl isobutyl ketone, methylpropyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachlorethane, ethyl ether, isopropyl ether, cyclohexane, cyclo-octane, benzene, toluene, naphtha, 1,4-dioxane, tetrahydrofuran, diglyme, water and mixtures thereof such as acetone and water, acetone and methanol, acetone and ethyl alcohol, methylene dichloride and methanol, and ethylene dichloride and methanol.

DESCRIPTION OF EXAMPLES OF THE INVENTION

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

A dispenser 10 for the controlled delivery of pyrantel tartrate is made as follows: first, 190 g of poly(2,2-dioxo-trans-1,4-cyclohexane dimethylene tetrahydrofuran) is heated in a laboratory Teflon ® pan equipped with a surface thermometer to about 150° C., and then 14 g of pyrantel tartrate is added thereto and the two components blended into a homogeneous composition. Next, the composition is molded into a cylindrical shape and cooled to room temperature. Then, the bioerodible composition is placed into a previously injected molded wide mouth dispenser-forming capsule shaped cellulose acetate butyrate member The dispenser is previously charged first with a 30 g stainless steel density member 18 adjacent to the bottom of dispenser 10, and overlayed with an expandable driving means 17. The driving means 17 comprises 2 g of sodium chloride and 5 g of the sodium salt of polyacrylic acid available as Carbopol ®, previously pressed into a tablet. The tablet is made using a 18.2 mm tableting tool and about 3½ tons of compression force. The tablet comprises a final shape that corresponds to the internal shape of the dispenser. Finally, the tip of the dispenser at the mouth is heated and curved inward to provide means for (a) breaking-up the solid carrier as it is pushed from dispenser 10 and for (b) aiding in avoiding a premature ejection of the carrier from the dispenser.

EXAMPLE 2

A dispenser is made according to the procedures set forth in Example 1, with the manufacturing conditions as set forth, except that in this example the pharmaceutically acceptable carrier comprises a condensation copolymer of 3,9-bis(ethylidine)-2,4,8,1O-tetraoxospiro[5,5]-undecane and ethylene glycol. The copolymer can be prepared according to the synthesis described in U.S. Pat. No. 4,304,767.

EXAMPLE 3

A dispenser system is prepared as follows: first the body section of a dispenser formed by injection molding cellulose acetate butyrate comprising a mouth, a lumen and a closed end is positioned with its mouth in an upright position, and a dense stainless steel element inserted into the hemispherical end of the body. The dense element is machined and it is shaped to match the internal shape of the body. Next, a layer of an expandable, swellable composition is charged on top of the dense element. The composition comprises 25% by weight of sodium chloride and 75% by weight of poly(ethylene oxide) having a molecular weight of about 200,000. The expandable ingredients are blended in a commercial blender with heat for 20 minutes to yield a homogeneous composition. The warm composition is charged into the body forming a layer that occupies ⅓ of the body. Next, a pharmaceutical carrier comprising the active agent is charged into the opened body. The carrier comprises 90 g of polylactide having a molecular weight of about 40,000 and 2.5 g of mebendazole. The carrier is prepared by dissolving in xylene the polylactide and adding thereto the mebendazole. The blended carrier is charged into the body to form a homogeneous mass and vacuum dried at 50° C. Then, a closure injected molded in the shape of a screen comprising plurality of cross strands defining a plurality of fragmenting member is adhesively sealed to the opening to yield the dispenser.

An embodiment of the invention pertains to a method for delivering a beneficial agent to an animal at a controlled rate, which method comprises the steps of: (A) admitting into an animal a dispensing device comprising: (1) a wall surrounding; (2) a lumen comprising a matrix stick that keeps its physical and chemical integrity in the lumen; (3) a beneficial drug in the matrix stick; (4) means in the lumen for pushing the carrier stick from the lumen; and (5) an opening in the wall comprising means for breaking the matrix stick from a first size to a second smaller size; (B) imbibing fluid through the wall into the lumen at a rate determined by the permeability of the wall and the osmotic pressure gradient across the wall to cause the means to take-up fluid, expand and push the matrix stick through the opening and concomitantly break the matrix stick from a first size to a smaller size; and thereby (C) deliver the beneficial agent to the animal over time.

Inasmuch as the foregoing specification comprises preferred embodiments of the invention, it is understood that variations and modifications may be made in accordance with the inventive principles disclosed, without departing from the scope of the invention.

We claim:

1. A dispenser for administering a beneficial agent formulation to an animal environment of use, the dispenser comprising:
 (a) a wall that surrounds and defines an internal lumen, the wall comprising at least in part a semipermeable composition that is permeable to the passage of fluid and is substantially impermeable to the passage of a beneficial agent;
 (b) carrier means in the lumen for administering a beneficial agent to the animal environment of use, said carrier means substantially maintaining its physical and chemical integrity while in the lumen of the dispenser;
 (c) a beneficial agent in the carrier means for administering a beneficial agent;
 (d) pushing means for occupying an increasing amount of space in the lumen for pushing the carrier means comprising the beneficial agent from the dispenser; and,
 (e) a mouth in the dispenser comprising means for breaking the carrier means from a first size to a second size as the carrier means leaves the dispenser.

2. The dispenser for administering the beneficial agent formulation to an animal environment of use according to claim 1, wherein the carrier means in the lumen for administering the beneficial agent comprises hydrophobic composition.

3. The dispenser for administering the beneficial agent formulation to an animal environment of use according to claim 1, wherein the carrier means in the lumen for administering the beneficial agent comprises a hydrophilic composition.

4. The dispenser for administering the beneficial agent formulation to an animal environment of use according to claim 1, wherein the carrier means in the lumen for administering the beneficial agent bioerodes in an animal environment of use.

5. The dispenser for administering the beneficial agent formulation to an animal environment of use according to claim 1, wherein the carrier means in the lumen for administering the beneficial agent is delivered from the dispenser and is hydrolyzed in the animal environment.

6. The dispenser for administering the beneficial agent formulation to an animal environment of use according to claim 1, wherein the carrier means in the lumen for administering the beneficial agent is delivered from the dispenser and is solubilized in the animal environment.

7. The dispenser for administering the beneficial agent formulation to an animal environment of use according to claim 1, wherein the carrier means in the lumen for administering the beneficial agent dissolves in an animal environment.

8. The dispenser for administering the beneficial agent formulation to an animal environment of use according to claim 1, wherein the carrier means in the lumen for administering the beneficial agent disintegrates in the animal environment.

9. The dispenser for administering the beneficial agent formulation to an animal environment of use according to claim 1, wherein the carrier means administers the beneficial agent by at least one process comprising diffusion, osmosis, osmotic bursting, solution leaching, solubilization, hydrolysis, enzymatic digestion, displacement and dissolution.

10. The dispenser for administering the beneficial agent formulation to an animal environment of use according to claim 1, wherein the animal environment of use is a ruminant.

11. The dispenser for administering the beneficial agent formulation to an animal environment of use according to claim 1, wherein the animal environment of use is a human.

12. A dispenser for administering a beneficial agent formulation to an animal environment of use, the dispenser comprising:

(a) a wall that surrounds and defines an internal lumen, the wall comprising at least in part a semipermeable composition that is permeable to the passage of fluid and is substantially impermeable to the passage of a beneficial agent;
(b) carrier means in the lumen for administering a beneficial agent to the animal environment of use, said carrier means substantially maintaining its physical and chemical integrity while in the lumen of he dispenser;
(c) a beneficial agent in the carrier means;
(d) push means for occupying an increasing amount of space in the lumen for pushing the carrier means for administering a beneficial agent from the dispenser;
(e) dense means in the lumen for maintaining the dispenser in the animal environment of use over time; and
(f) an opening in the wall of the dispenser for communicating the carrier means for administering the beneficial agent with the environment of use, said opening comprising means for breaking the carrier means into smaller carrier means as the carrier means leaves the dispenser.

13. A dispenser for administering a beneficial agent formulation to an animal environment of use, the dispenser comprising:
(a) a wall that surrounds and defines an internal lumen, the wall comprising at least in part a semipermeable composition that is permeable to the passage of fluid and is substantially impermeable to the passage of a beneficial agent;
(b) carrier means in the lumen for housing a beneficial agent formulation, said carrier means maintaining its physical and chemical integrity while the carrier means is in the lumen of the dispenser;
(c) a beneficial agent formulation in the carrier means;
(d) expandable means for occupying an increasing amount of space in the lumen for pushing the carrier means from the lumen, said expandable means comprising a hydrophilic polymeric composition; and,
(e) a mouth in the dispenser comprising means for fragmenting the carrier means from its lumen size to a different size as it leaves the dispenser.

14. The dispenser for administering the beneficial agent formulation according to claim 14, wherein the means for fragmenting the carrier means is serrated.

15. The dispenser for administering the beneficial agent formulation according to claim 14, wherein the means for fragmenting the carrier means is saw-toothed.

16. The dispenser for administering the beneficial agent formulation according to claim 14, wherein the means for fragmenting the carrier means is a screen.

17. The dispenser for administering the beneficial agent formulation according to claim 14, wherein the means for fragmenting the carrier means comprises a cutting edge.

18. The dispenser for administering the beneficial agent formulation according to claim 14, wherein the means for fragmenting the carrier means comprises at least one string formed of naturally occurring or synthetic materials.

19. A dispenser for administering beneficial agent formulation to an animal environment of use, the dispenser comprising:
(a) a wall that surrounds a lumen, the wall comprising a semipermeable composition permeable to the passage of fluid;
(b) carrier means in the lumen for containing a beneficial agent formulation, said carrier means keeping its physical and chemical integrity while the carrier means is in the lumen;
(c) a beneficial agent formulation in the carrier means;
(d) solution means for occupying an increasing amount of space in the lumen for pushing the carrier means from the lumen, said solution means comprising an osmagent that imbibes fluid into the lumen and forms a solution; and,
(e) an opening in the dispenser comprising means for fragmenting the carrier means from its lumen size to a fragmented size as the carrier means is pushed from the dispenser.

20. A dispenser for administering a beneficial agent formulation to an animal environment of use, the dispenser comprising:
(a) a wall that surrounds a lumen, the wall comprising a semipermeable composition permeable to the passage of fluid;
(b) carrier means in the lumen for housing a beneficial agent formulation, said carrier means keeping its physical integrity in the lumen;
(c) a beneficial agent formulation in the carrier means;
(d) gas generating means for occupying an increasing amount of space in the lumen for pushing the carrier means from the lumen; and,
(e) an opening in the dispenser comprising means for fragmenting the carrier means from its lumen size to a fragmented size as the carrier means is pushed from the dispenser.

21. A method for delivering a beneficial agent to an animal, wherein the method comprises:
(a) admitting into an animal a dispensing device comprising:
(1) a wall;
(2) a lume defined by the wall;
(3) a solid matrix in the lumen, which matrix comprises compositional means keeping its physical and chemical integrity while in the lumen;
(4) a beneficial agent in the matrix;
(5) an opening in the wall;
(6) means in the opening for changing the matrix from a first size to a second size;
(7) means in the lumen for pushing the matrix through the opening;
(b) pushing the matrix through the opening for changing it from a first to a second size; thereby,
(c) delivering the beneficial agent to the animal over time.

* * * * *